United States Patent [19]
Paul et al.

[11] Patent Number: 6,130,049
[45] Date of Patent: Oct. 10, 2000

[54] ASSAY METHODS AND KITS FOR DIAGNOSING AUTOIMMUNE DISEASE

[75] Inventors: Sudhir Paul; Ravishankar Kalaga, both of Omaha, Nebr.

[73] Assignee: The Board of Regents of the University of Nebraska, Lincoln, Nebr.

[21] Appl. No.: 08/983,485

[22] PCT Filed: Jul. 19, 1996

[86] PCT No.: PCT/US96/12026

§ 371 Date: Jan. 21, 1998

§ 102(e) Date: Jan. 21, 1998

[87] PCT Pub. No.: WO97/04125

PCT Pub. Date: Feb. 6, 1997

Related U.S. Application Data

[60] Provisional application No. 60/001,370, Jul. 21, 1995.

[51] Int. Cl.[7] ............................................. C12Q 1/00
[52] U.S. Cl. ............................ 435/7.1; 435/7.6; 435/975; 435/188.5
[58] Field of Search ................................ 435/7.1, 7.6, 975, 435/188.5

[56] References Cited

PUBLICATIONS

Paul, S., et al. (1997) J. Immunol. 159(3), 1530–1536.
Kalaga, R, et al. (1995) J. Immunol. 155(5), 2695–2702.
Li, L, et al. (1995) J. Immunol. 154(7), 3328–3332.

*Primary Examiner*—Charles L. Patterson, Jr.
*Attorney, Agent, or Firm*—Dann, Dorfman, Herrell and Skillman

[57] ABSTRACT

The present invention provides assay methods and kits for detecting the existence of, or the propensity toward the development of autoimmune diseases, such as rheumatoid arthritis, systemic lupus erythematosus, autoimmune thyroiditis, Birdshot retinopathy and anti-coagulant deficiency due to autoantibodies.

35 Claims, 6 Drawing Sheets

ASSAY METHODS AND KITS FOR DIAGNOSING AUTOIMMUNE DISEASE

This application is a 371 of PCT/US96/12026 filed Jul. 19, 1996 and claims benefit to U.S. provisional application Ser. No. 60/001,370 filed Jul. 21, 1995.

FIELD OF THE INVENTION

This invention provides assay methods and kits for detecting the existence of or propensity toward developing autoimmune disease. Specifically, methodology is provided for performing a simple test on a biological fluid that will facilitate the identification of patients afflicted with or at risk for developing autoimmune disorders such as rheumatoid arthritis, systemic lupus erythematosus, autoimmune thyroiditis, Birdshot retinopathy and anti-coagulant deficiency due to autoantibodies.

BACKGROUND OF THE INVENTION

A key attribute of the immune system is the discrimination between self and non-self antigens. Surface recognition molecules on lymphocytes are sufficiently diverse for any antigen to find some lymphoid cells with surface antibody or T-cell receptor whose binding constant for antigen is high enough to lead to activation, thereby inducing the clonal expansion of cells recognizing that antigen. When these activated cell types (B and T cells) synthesize molecules (antibodies, T cell receptors) that react with self antigens, they are eliminated from the body. Immunologists refer to the inability to produce substances that react with self antigens as tolerance. The mechanisms that give rise to tolerance are poorly understood but involve rendering unreactive the clones of both B and T cells that would otherwise carry out anti-self reactions.

The immune system in mice becomes responsive to foreign antigens in the days just after birth. All antigens present in the body at the time the system matures are considered by the immune system to be self. Thus if foreign antigens are incorporated into a newborn mouse, subsequent challenge with the same antigen will not induce an immune response. Because new clones of lymphocytes appear in an animal throughout its life, the tolerance to self must be an active, ongoing process. Suppressor T lymphocytes are thought to play an important role in maintaining tolerance by specifically suppressing lymphocyte clones that react against self-antigens.

The consequences of the failure of tolerance can be severe. It is well known that certain autoimmune diseases are associated with autoantibodies directed against hormones and cell surface antigens. Examples of these diseases and associated antigens include the following:

| AUTOINMUNE DISEASE | ASSOCIATED ANTIGEN |
| --- | --- |
| Diabetes | insulin, insulin receptor, glutamate decarboxylase |
| Myasthenia gravis | acetylcholine receptor |
| Autoimmune thyroiditis | thyroglobulin, thyroid peroxidase |
| Systemic lupus erythmatosus (SLE) | small nuclear RNA, DNA and histones, phospholipids |
| Pernicious anemia | gastric parietal cell associated antigens |
| Rheumatoid arthritis | collagen, IgG |
| Wegener's Granuloma | proteinase 3 |
| Biliary cirrhosis | pyruvate dehydrogenase |

Related diseases, in the sense of having autoimmune disease-like components or mechanisms, include asthma and acquired immunodeficiency syndrome. Relevant antigens recognized by antibodies in these disorders are VIP (asthma), and neurolikin, VIP, HLA antigens and DNA (HIV).

Tissue injury in autoimmune disease occurs by several humoral and cell-mediated mechanisms. Autoantibodies alone can cause certain diseases, e.g., myasthenia gravis and Graves disease, as demonstrated by adoptive transfer via administration of antibodies in animal models. Rose, N. R. and I. R. Mackay, Editors. *The Autoimmune Diseases.* Orlando: Academic Press, Inc., 1985. In other diseases, tissue damage is believed to occur by a combination of autoantibodies, lymphocyte and macrophage infiltration, and the release of inflammatory mediators, including proteases.

Antibodies can recognize small arrays of atoms as well as large epitopes composed of as many as 25 amino acid residues. The target molecule for an antibody could be a small hapten or a macromolecule like a protein or nucleic acid.

Antigen recognition by antibodies occurs at complementarity determining regions (CDRs) encoded by V (variable), D (diversity) and J (joining) genes. There are three CDRs each in the variable regions of H- and L-chains ($V_H$, $V_L$). The immune system possesses the ability to diversify $V_H$ and $V_L$ sequences, permitting generation of $10^{10}$–$10^{12}$ antibody combining sites. Diversification occurs by V—D—J gene rearrangements, mutations in V-genes (mutation rate $10^{-3}$–$10^{-4}$/base pair/cell division$^1$), and combinatorial variation due to pairing of individual $V_L$ and $V_H$ domains from the available genes (>300 and >1000, respectively). This sequence diversification allows for the evolution of new functions in antibodies, including catalysis. Homologies between trypsin, in particular the sequence surrounding the active site serine, with antibody L-chains are described. Erhan, A. and L. D. Greller, Do immunoglobulins have proteolytic activity? *Nature*. 251: 353–355, 1974. Efficient proteolysis by human autoantibodies to the bronchodilator peptide vasoactive intestinal peptide (VIP) has been observed (Paul, S., D. J. Volle, C. M. Beach, D. R. Johnson, M. J. Powell, and R. J. Massey, Catalytic hydrolysis of vasoactive intestinal peptide by human autoantibody, *Science*, 244: 1158–1162, 1989; and Paul, S., M. Sun, R. Mody, S. H. Eklund, C. M. Beach, R. J. Massey, and F. Hamel, Cleavage of vasoactive intestinal peptide at multiple sites by autoantibodies, *J. Biol. Chem.*, 266: 16128–16134, 1991), as well as with monoclonal antibodies (Paul, S., M. Sun, R. Mody, H. K. Tewary, and A. Tramontano, Peptidolytic monoclonal antibody elicited by a neuropeptide, *J. Biol. Chem.*, 267: 13142–13145, 1992) and a recombinant antibody light chain raised by immunization with VIP. Gao, Q., M. Sun, S. Tyutyulkova, A. Tramontano, R. J. Massey, and S. Paul, Substrate-driven formation of a proteolytic antibody light chain, Abstract presented at New York Academy of Sciences Conference on *Immunoglobulin Gene Expression in Development and Disease,* Montreal, Canada, Jul. 13–17, 1994. An autoantibody to thyroglobulin has also been shown to cleave thyroglobulin. Paul, S., L. Li, S. Tyutyulkova, M. D. Kazatchkine, and S. Kaveri, Catalytic activity of anti-thyroglobulin antibodies, Abstract presented at New York Academy of Sciences Conference on *Immunoglobulin Gene Expression in Development and Disease,* Montreal, Canada, Jul. 13–17, 1994. Autoantibody catalyzed hydrolysis of VIP has been independently reproduced (Suzuki, H., H. Imanishi, T. Nakai, and Y. K. Konishi, Human autoantibodies that catalyze the hydrolysis of vasoactive intestinal polypeptide, *Biochem (Life Sci. Adv.).* 11: 173–177, 1992)

and other groups have shown autoantibody mediated hydrolysis of DNA (Shuster, A. M., G. V. Gololobov, O. A. Kvashuk, A. E. Bogomolova, I. V. Smirnov, and A. G. Gabibov. DNA hydrolyzing autoantibodies, Science, 256: 665–667, 1992) and a cholinesterase activity associated with an anti-idiotypic antibody to anti-cholinesterase (Izadyar, L., A. Friboulet, M. H. Remy, A. Roseto, and D. Thomas, Monoclonal anti-idiotypic antibodies as functional internal images of enzymes active sites: Production of a catalytic antibody with a cholinesterase activity, Proc. Natl. Acad. Sci. USA., 90: 8876–8880, 1993).

Catalytic antibodies such as those discussed above are likely to cause more harm than non-catalytic antibodies. Clinical data suggest that certain autoimmune disorders may be caused by catalytic autoantibodies directed against nucleic acids, key regulatory proteins (i.e., insulin, glucagon, prolactin, VIP, substance P, blood clotting factors) and the cell surface receptors for these agents.

The presence of autoantibodies, however, is not an unequivocal sign of an autoimmune disease. This classification, in fact, is generally restricted to those cases in which the autoimmune reaction is the cause of tissue damage, either systemic or organ specific.

To date, autoimmune diseases have been linked to a defect of the immune system. Methods that facilitate the identification of patients who may be predisposed to autoimmune disorders are highly desirable so that early preventative treatments may be obtained.

SUMMARY OF THE INVENTION

A simple assay is provided that will rapidly and reproducibly facilitate the diagnosis of those patients afflicted with an autoimmune disease and those who may have a propensity toward such disease. In contrast to the approaches used in the past, the present invention is based on the concept that one of the pathogenic factors of autoimmune disorders is a decrease in the activity of poly-reactive or non-antigen specific catalytic antibodies in autoimmune disease sufferers as compared to healthy patients. An additional pathogenic factor in autoimmunity is the relative increase in the activity of catalytic antibodies specific for individual antigens associated with autoimmune disease such as thyroglobulin and vasoactive intestinal peptide.

The determination of altered levels of the above-described catalytic antibody interactions relative to the same interactions in healthy controls facilitates the diagnosis of those afflicted with or having a propensity toward autoimmune disease.

According to one embodiment, the method of the invention is carried out by providing, as a test sample, a specimen of biological fluid from a patient, which specimen is suspected of containing catalytic antibodies; providing, as a control sample, a specimen of biological fluid from a healthy individual; contacting a peptide, comprising amino acid residues selected from the group consisting of at least one basic amino acid, proline or a combination thereof, with the test sample and with the control sample; subjecting the peptide-containing test sample and control sample to conditions promoting catalytic cleavage of the peptide by any catalytic antibodies present in the samples; and measuring the relative activity of any catalytic antibodies in the test sample and said control sample, as determined by the presence of cleavage products formed from the peptide. The measurement of depressed polyreactive activity of catalytic antibodies in the test sample relative to the control sample is indicative of autoimmune disease or predisposition to such disease in the patient.

In another embodiment, the same general procedure as that just described is followed, except that the test sample and control sample are contacted with an autoimmune disease-associated antigen, or with a fragment thereof, with the relative activity of catalytic antibodies in the samples being measured by determining the presence of cleavage product formed from the autoimmune disease-associated antigen or fragment. In this particular embodiment, the measurement of elevated activity of catalytic antibodies in the test sample relative to the control sample is indicative of the disorder sought to be diagnosed.

The above described diagnostic methods can be performed concomitantly, i.e., measuring the relative activity of catalytic antibodies in aliquots of the test sample and of the control sample by determining the presence of cleavage products formed from both the peptide and the autoimmune disease associated antigen or fragment, so as to provide an indication of the existence of, or predisposition to autoimmune disease in the subject undergoing diagnosis.

Another aspect of the invention is a kit of materials useful in performing the method of the invention. A first kit according to the invention may comprise predetermined amounts of a peptide comprising amino acid residues selected from the group consisting of at least one basic amino acid, proline or combination thereof and a reagent for detection of at least one cleavage product of the peptide. A second kit according to the invention may comprise predetermined amounts of an autoimmune disease-associated antigen and a reagent for detection of at least one cleavage product of the autoimmune disease-associated antigen. In either kit, the amounts of peptide, autoimmune disease-associated antigen and detection reagent(s), as the case may be, must be sufficient for performing the desired diagnosis.

When diagnosis is based on concomitant measurement of catalytic antibody activity, as based on the determination of cleavage products formed from both the above-described peptides and autoimmune disease-associated antigens or fragments, the materials required for such diagnosis may conveniently be packaged in a single kit.

The methods and kits of the invention are particularly useful for the diagnosis of rheumatoid arthritis, systemic lupus erythematosus, Hashimoto's thyroiditis and asthma.

DETAILED DESCRIPTION OF THE INVENTION

Figure 1:
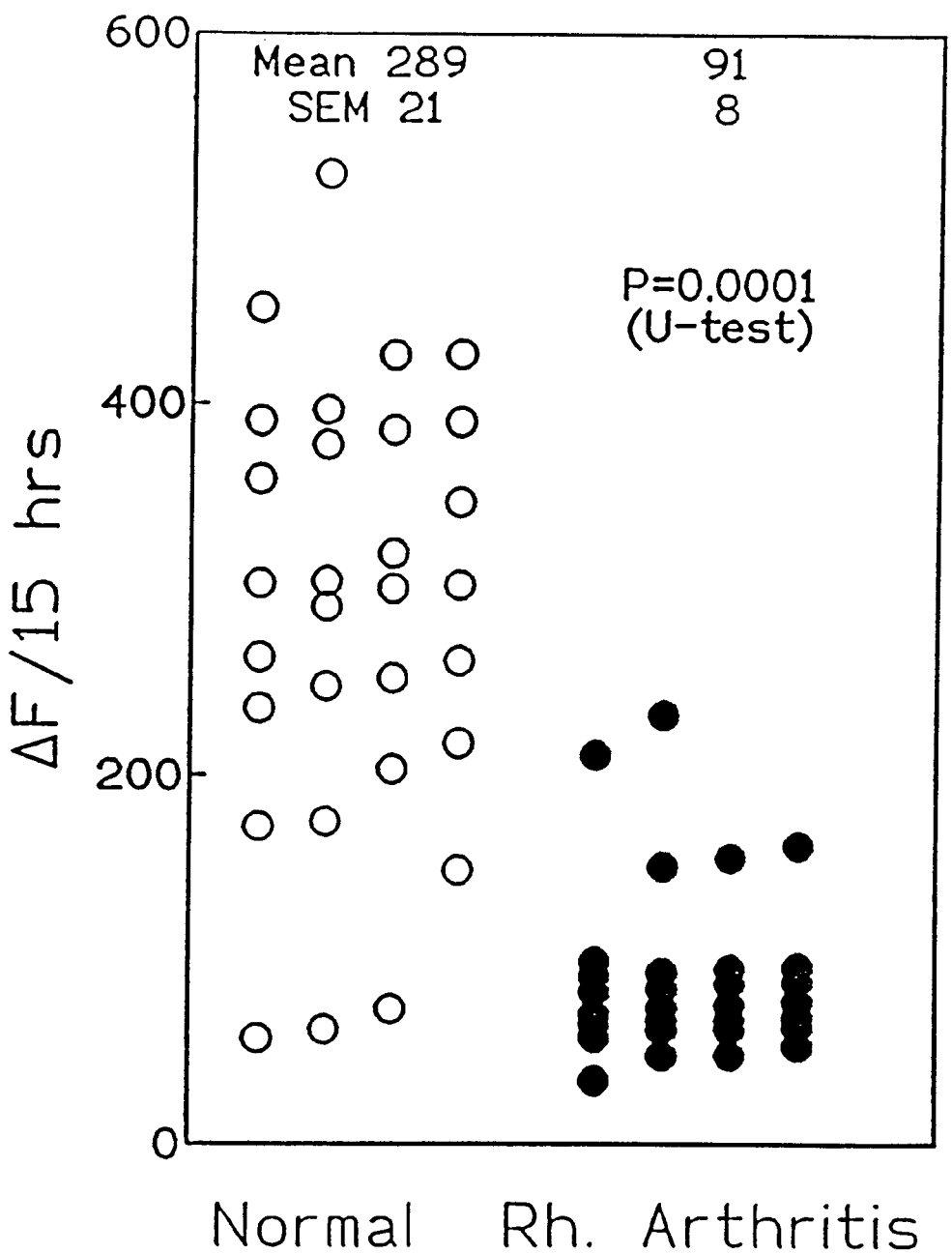
FIG. 1 is a graph depicting peptide-MCA cleaving activities in IgG from healthy subjects and rheumatoid arthritis patients (N=30 of each group).

The diagnostic procedure of the invention is based in part, on the observation that serum of healthy subjects contain catalytic antibodies that cleave surrogate peptide bonds at basic residues and at proline. The cleavage reaction is polyreactive, since the primary determinant in the substrate peptide is simply the presence of bonds between basic residues and/or proline. Additionally, several substrates with varying flanking residues are utilized by the antibodies. Polyreactive catalytic antibody activity is decreased in serum of patients having autoimmune diseases, thus providing one diagnostic indicator of the presence of such disease.

In contrast to the polyreactive catalytic activity, the activity of antibodies specific for individual autoimmune disease-associated antigens, such as VIP and thyroglobulin, or fragments of such antigens is increased in serum of patients having the autoimmune disease. This finding provides the second diagnostic indicator of the presence of, or predisposition toward such disease.

The diagnostic method of the invention involves the measurement of polyreactive and antigen specific catalytic antibody activity in biological fluid specimens of patients suspected of having an autoimmune disease. A decrease in polyreactive activity, and/or increase in antigen-specific activity relative to healty individuals, indicates the presence of the autoimmune disease, or the propensity to develop such disease.

The following definitions are provided to aid in the understanding of the subject matter of the present invention:

Antibody: An immunoglobulin molecule with a specific amino acid sequence evoked in man or other animals by an antigen, and characterized by reacting specifically with the antigen in some demonstrable manner, antibody being defined in terms of its conjugate antigen and vice versa. Components of antibodies have also been shown to possess catalytic activity. These include Fab fragments, light chains, light chain dimers, Fd fragments, and mixtures of Fd fragments and light chains.

Catalytic Antibody: An antibody as described above which mediates the cleavage of its target antigen.

Polyreactive antibody: Antibodies which bind antigen with low affinity; such antibodies are polyreactive in the sense that multiple antigens with little or no structural similarity bind the same antibody (e.g., peptides, DNA and lipids). These are sometimes referred to as "natural antibodies" in that they are not elicited in a specific response to antigenic challenge. Grabar (Grabar, P. Autoantibodies and the physiological role of immunoglobulins, *Immunol. Today*, 4: 337–340, 1983) has hypothesized that such antibodies fulfil a housekeeping role in metabolic clearance of autoantigens by mechanisms such as immune complex ingestion by macrophages.

Antigen specific antibodies: Unlike natural antibodies, these antibodies bind target antigens with high affinity and their concentrations are elevated in autoimmune disease. They may also be autocatalytic.

Autoimmmunity: In immunology, the condition in which one's own tissues are subject to deleterious effects of the immune system, as in autoimmune disease and autoallergy.

Patient: A patient may be a human being or animal.

Healthy Individual: An individual who, according to medically acceptable procedure, has been shown not to have an autoimmune disease.

Kits provided for practicing the diagnostic methods of the invention include specific antigens (VIP, Tg and the like) and general antigens (peptide-MCA and the like) for use as substrates for antigen specific catalytic antibodies and polyreactive catalytic antibodies, as well as control catalytic antibodies against selected polypeptide substrates.

The kits will also typically include a reagent for detection of a cleavage product for the polyreactive peptide or autoimmune disease-associated antigen, as the case may be. The detection reagent preferably comprises an antibody which is capable of binding specifically to such cleavage product and which is conjugated to a detectable label. Suitable labels for this purpose are substances selected from the group consisting of molecules or ions directly or indirectly detectable based on light absorbance, fluorescence, phosphorescence, luminescence, or acoustic properties; molecules or ions detactable by their radioactive property; and molecule or ions detectable by their nuclear magnetic resonance or paramagnetic properties. Detection of cleavage products may be conveniently carried out by means of an enzyme label which acts on a substrate, which is also provided in the kit, to produce a spectrally measurable product. The kit of the invention may also conveniently include a device for purifying biological samples, together with various solutions which may be used in performing the diagnostic procedure, such as buffer(s), saline, diluent, controls and the like.

Methods are also provided for isolating proteolytic antibodies against any polypeptide substrate from the pre-existing and induced repertoires. The pre-existing repertoires are those found in healthy individuals and autoimmune disease patients; the induced repertoire consists of polyclonal antibodies, cell lines and antibody genes derived from animals immunized with any selected antigen. Based on the ever-accumulating demonstrations of catalytic hydrolysis of several proteins by polyclonal antibodies, as well as by antibodies from phage display libraries and antibody subunits from multiple myeloma patients, it is now within the level of ordinary skill in the art to isolate catalytic antibodies specific for virtually any polypeptide antigen by carefully screening the immune repertoire.

General methods for catalytic antibody isolation are described in the following references: Li et al., Methods of Measuring thyroglobulin and peptide-methylcoumarinamide hydrolysis by autoantibodies, in *Antibody Engineering Protocols,* S. Paul, Ed. (Methods in Molecular Biology Series, Humana Press, Totowa, N.J.) 51: 417–422 (1995); Huang et al., Assays of radiolabelled VIP binding and hydrolysis by antibodies, in *Antibody Engineering Protocols,* S. Paul, Ed. (Methods in Molecular Biology Series, Humana Press, Totowa, N.J.) 51: 409–416 (1995).

To summarize these methods, in the case of large polypeptides, the substrate is prepared by radiolabeling with an appropriate radioisotope or any detectable label. The labeled substrate is purified and incubated with antibodies from the various sources described above and hydrolysis of the substrate is determined by standard methods, such as SDS-electrophoresis and autoradiography. Appearance of labeled bands with molecular weight lower than the substrate is indicative of antibody-mediated catalysis. Hydrolysis of mid-sized peptides is easily accomplished by the trichloroacetic acid precipitation method, as described for radiolabeled VIP in the above reference. Fluorescent labels can be attached to the substrate, as described by Kalaga et al., *J. Immunol.*, 155:2695–2702 (1995) and Paul et al., *J. Biol. Chem.* 267: 13142–13145 (1992). These methods are generally applicable, as long as attachment of labels to the substrate does not interfere with recognition by catalytic antibodies. Once suitable labeled substrates are produced, assay of their hydrolysis is straightforward and large numbers of samples can be screened for catalytic antibody activity for the purpose of identifying efficient catalysts.

The diagnostic methods of the invention may also be performed on solid supports, such as polystyrene plates and/or nitrocellulose. A suitable substrate with a detectable label may be adsorbed to or covalently linked to a solid support. In one embodiment of the invention, the action of the catalytic antibody removes the detectable label from the substrate and activity is measured by a loss of signal relative to a control sample.

The following examples describe preferred methods for performing the diagnostic procedures of the present invention. Although certain antigenic substrates such as vasoactive intestinal peptide, thyroglobulin, and peptide-MCA analogs are utilized in the following examples, it will be appreciated by those skilled in the art that the methods of the invention may be performed on a variety of other antigenic substrates.

EXAMPLE I

DETECTION OF POLYREACTIVE ANTIBODIES

The experimental results set forth hereinbelow indicate that antibodies possess a catalytic activity unrelated to their high affinity antigen binding activity. Since antibodies are present at a concentration of about 70 $\mu$M in blood, even kinetically inefficient catalysis could be functionally important. Several observations suggest that low affinity antigen-nonspecific catalysis by natural polyreactive antibodies found in healthy individuals prevents accumulation of autoantigens to a level permitting a massive autoimmune response.

Although antibodies have traditionally been viewed as high affinity binding reagents, it is now recognized that they can develop catalytic functions akin to enzymes. Subpopulations of high affinity autoantibodies to polypeptide (Paul, S., D. J. Volle, C. M. Beach, D. R. Johnson, M. J. Powell, and R. J. Massey, Catalytic hydrolysis of vasoactive intestinal peptide by human autoantibody, *Science*, 244: 1158–1162 (1989); Paul, S., M. Sun, R. Mody, S. H. Eklund, C. M. Beach, R. J. Massey, and F. Hamel, Cleavage of vasoactive intestinal peptide at multiple sites by autoantibodies, *J. Biol. Chem.*, 266: 16128–16134 (1991); Suzuki, H., H. Imanishi, T. Nakai, and Y. K. Konishi, Human autoantibodies that catalyze the hydrolysis of vasoactive intestinal polypeptide, *Biochem. (Life Sci. Adv.)*, 11: 173–177 (1992); and Li, L., S. Paul, S. Tyutyulkova, M. Kazatchkine, and S. Kaveri, Catalytic activity of anti-thyroglobulin antibodies, *J. Immunol.*, 154: 3328–3332 (1995)) and nucleic acid antigens (Shuster, A. M., G. V. Gololobov, O. A. Kvashuk, A. E. Bogomolova, I. V. Smirnov, and A. G. Gabibov, DNA hydrolyzing autoantibodies, *Science*, 256: 665–6617 (1992)) and antibodies elicited by experimental immunization with a polypeptide (Paul S., M. Sun, R. Mody, H. K. Tewary, S. Mehrotra, T. Gianferrara, M. Meldal, and A. Tramontano, Peptidolytic monoclonal antibody elicited by a neuropeptide, *J. Biol. Chem.*, 267: 13142–13145 (1992)) are described to possess catalytic activity. Germ-line antibody sequences undergo extensive diversification over the course of affinity maturation of antibody responses, leading to the elaboration of a binding site capable of accommodating specific ligands with high affinity. Catalytic activity has been observed until now only in mature, high affinity antibodies (Paul, S., D. J. Volle, C. M. Beach, D. R. Johnson, M. J. Powell, and R. J. Massey, Catalytic hydrolysis of vasoactive intestinal peptide by human autoantibody, *Science*, 244: 1158–1162 (1989); Paul, S., M. Sun, R. Mody, S. H. Eklund, C. M. Beach, R. J. Massey, and F. Hamel, Cleavage of vasoactive intestinal peptide at multiple sites by autoantibodies, *J. Biol. Chem.* 266:16128–16134 (1991); Suzuki, H., H. Imanishi, T. Nakai, and Y. K. Konishi, Human autoantibodies that catalyze the hydrolysis of vasoactive intestinal polypeptide, *Biochem. (Life Sci. Adv.)*, 11: 173–177 (1992); Li, L., S. Paul, S. Tyutyulkova, M. Kazatchkine, and S. Kaveri, Catalytic activity of anti-thyroglobulin antibodies, *J. Immunol.*, 154: 3328–3332 (1995); Shuster, A. M., G. V. Gololobov, O. A. Kvashuk, A. E. Bogomolova, I. V. Smirnov, and A. G. Gabibov. DNA hydrolyzing autoantibodies, *Science*, 256: 665–6617 (1992); Paul S., M. Sun, R. Mody, H. K. Tewary, S. Mehrotra, T. Gianferrara, M. Meldal, and A. Tramontano, Peptidolytic monoclonal antibody elicited by a neuropeptide, *J. Biol. Chem.*, 267: 13142–13145 (1992); Gao, Q.-S., M. Sun, S. Tyutyulkova, D. Webster, A. Rees, A. Tramontano, R. Massey, and S. Paul, Molecular cloning of a proteolytic antibody light chain, *J. Biol. Chem.*, 269: 32389–32393 (1994); and Izadyar, L., A. Friboulet, M. H. Remy, A. Roseto, and D. Thomas, Monoclonal anti-idiotypic antibodies as functional internal images of enzyme active sites: Production of a catalytic antibody with a cholinesterase activity, *Proc. Natl. Acad. Sci. USA*, 90: 8876–8880 (1993)), but it is not known whether elements of the catalytic site are already present in germ-line antibody sequences or are developed de novo during somatic mutation and V—D—J/V—J rearrangement.

Specific catalytic antibody fragments to VIP[3] (Gao, Q.-S., M. Sun, S. Tyutyulkova, D. Webster, A. Rees, A. Tramontano, R. Massey, and S. Paul, 1994, Molecular cloning of a proteolytic antibody light chain, *J. Biol. Chem.*, 269: 32389–32393 (1994)) and autoantibodies to thyroglobulin (Li, L., S. Paul, S. Tyutyulkova, M. Kazatchkine, and S. Kaveri, Catalytic activity of anti-thyroglobulin antibodies, *J. Immunol.*, 154: 3328–3332 (1995)) are capable of low affinity recognition and slow hydrolysis of generic protease substrates containing basic amino acids. These observations provided the impetus for use of these substrates as probes to study the association of antibody catalysis with autoimmune disease. Patients with rheumatoid arthritis were selected for this study, since increased levels of autoantibodies to a variety of antigens are found in this disease (Snyderman, R., Humoral Immunity, In *Rheumatoid Arthritis*. P. D. Utsinger, N. J. Zvaifler, and G. E. Ehrlich, eds. J.B. Lippincott Company, Philadelphia, Pa. p. 243–249 (1985)).

Contrary to the initial expectations, catalytic activity detected using generic peptide substrates was observed in IgG from healthy humans and unimmunized mice, while it was markedly diminished in rheumatoid arthritis patients. Immunization of mice with SRBC or gp120 also resulted in decreased activity levels, suggesting that the activity is negatively correlated with vigorous immune responses. The activity is designated 'polyreactive' because peptides with different sequences may be utilized as substrates.

I. Human Subjects: Rheumatoid arthritis patients (N=30), osteoarthritis patients (N=5) and healthy volunteers (N=30)

were of either sex with mean (±SEM) ages 47±2.0, 59±7.6 and 36±1.3 years, respectively. Rheumatoid arthritis and osteoarthritis patients were from the rheumatology clinic at the University of Nebraska Medical Center, and fulfilled American College of Rheumatology diagnostic criteria (Arnett, F. C., S. M. Edworthy, D. A. Bloch, D. J. McShane, J. F. Fries, N. S. Cooper, L. A. Healey, S. R. Kaplan, M. H. Liang, H. S. Luthra, T. A. Medsger, Jr., D. M. Mitchell, D. H. Neustadt, R. S. Pinals, J. G. Schaller, J. T. Sharp, R. L. Wilder, and G. G. Hunder, The American Rheumatism Association 1987 revised criteria for the classification of rheumatoid arthritis, *Arthritis Rheum.*, 31: 315–324 (1988). At the time of the blood draw, twenty-three rheumatoid arthritis patients were being treated with a nonsteroidal anti-inflammatory agent, methotrexate, hydroxychloroquine or sulfasalazine, or combinations thereof. The remaining seven patients were not receiving drug treatment. Healthy control volunteers denied any history of rheumatological, respiratory, cardiovascular, gastrointestinal, reproductive or nervous system abnormalities.

II. IgG and Fab Preparation: IgG samples were purified by ammonium sulfate precipitation of plasma or serum and chromatography on protein-G Sepharose (Pharmacia) in disposable polypropylene columns (0.6×5 cm) by gravity flow at a stoichiometry of 0.1 ml plasma per 0.2 ml gel (Paul, S., M. Sun, R. Mody, S. H. Eklund, C. M. Beach, R. J. Massey, and F. Hamel, Cleavage of vasoactive intestinal peptide at multiple sites by autoantibodies, *J. Biol. Chem.*, 266: 16128–16134 (1991)). Following passage of samples through the columns, they were washed with 2 ml 50 mM Tris-HCl, 0.02% sodium azide, pH 7.4 and bound IgG was eluted with 0.8 ml 100 mM glycine-HCl, pH 2.7 into collection tubes containing 0.04 ml 1 M Tris-HCl, pH 9.0. The volumes of wash and elution buffers were sufficient to remove unbound proteins and elute the bound IgG fraction, respectively, shown by restoration of effluent protein absorbance at 280 nm to baseline values in pilot chromatography experiments. Ten columns were run simultaneously. The resultant IgG preparations were electrophoretically homogeneous (Paul, S., M. Sun, R. Mody, S. H. Eklund, C. M. Beach, R. J. Massey, and F. Hamel, Cleavage of vasoactive intestinal peptide at multiple sites by autoantibodies, *J. Biol. Chem.*, 266: 16128–16134 (1991)) and contained a single heavy chain band (approximately 60 kD) and a single light chain band (approximately 25 kD). Gel filtration of the IgG (2 mg) was in 6 M GdnCl (Sigma), pH 6.5, on a Superose-12 FPLC column (Pharmacia). Pooled fractions corresponding to the optical density peak ($A_{280}$; elution volume 7.5 ml–8.5 ml) were rechromatographed in 6 M GdnCl, pH 6.5, on the same column and the fractions were renatured by dialysis against 50 mM Tris-HCl, 100 mM glycine, 0.025% Tween-20, 0.02% sodium azide, pH 7.7 for 2 days with 4 buffer changes using a GIBCO multi-well dialysis device (final guanidine concentration <1 nM assuming equilibration across the dialysis membrane). Fab fragments were prepared by papain digestion of IgG, inactivation of papain with iodoacetamide and purification on immobilized protein A and Superose-12 columns (Sun, M., B. Mody, S. H. Eklund, and S. Paul, VIP hydrolysis by antibody light chains, *J. Biol. Chem.*, 266: 15571–15574 (1991)). The Fab fragments were composed of a single 50 kD band analyzed by nonreducing SDS-electrophoresis.

III. Catalysis Assays: Antibody fractions were mixed with peptide-methylcoumarinamide substrates (Peptides International or Sigma) in 60 μl 50 mM Tris--HCl, 100 mM glycine, 0.025% Tween-20, pH 7.7 buffer in 96-well plates (MicroFluor W, Dynatech) and incubated at 37° C. in a humidified incubator. Hydrolysis of the peptide-MCA substrates was determined as the fluorescence of the leaving group (aminomethylcoumarin; $\lambda_{em}$ 460 nm, $\lambda_{ex}$ 370 nm) using a plate reader (Perkin Elmer LS50 fluorimeter). The concentration of the product was computed by comparison of the fluorescence yield using aminomethylcoumarin (Peptides International) measured in identical volumes (21.9 FU/μM/60 μl). Initial rate data measured at varying substrate concentration were fitted to the Michaelis-Menten-Henri equation using Enzfitter (Elsevier-Biosoft). Some assays were done using immobilized IgG as catalyst. Multiscreen 96-well plates fitted with filters (Millipore DV) were treated with 3% BSA in water (15 min), 40 μl protein G-Sepharose (settled volume; 0.72 mg IgG binding capacity) and 30 μg IgG (20 μl) were co-incubated in the wells (1 h, 4° C. with shaking), the gel washed six times with 200 μl 50 mM Tris-HCl, 100 mM glycine and then incubated with 60 μl substrate solution (500 μM) at 37° C. The gel was permitted to settle at the end of the incubation, 30 μl of the fluid transferred to 96-well MicroFluor W plates and fluorescence was measured. Background fluorescence measured in wells containing the substrate in diluent was generally less than 10 FU and was subtracted from values observed in the presence of catalyst. Hydrolysis of synthetic Pro-Phe-Arg-Phe (peptide content, 76%) by IgG (63 μg) immobilized on protein G-Sepharose (150 μl settled gel) was determined by removal of the supernatant following incubation at 37° C. and separation by reversed-phase HPLC on a Novapak C18 column fitted with a guard column (Guard-Pak™, Waters) using a gradient of solvent B (0.1% trifluoroacetic acid in 80% acetonitrile in water) in solvent A (0.1% trifluoroacetic acid in water) (0–30% solvent B, 65 min) (Paul, S., M. Sun, R. Mody, S. H. Eklund, C. M. Beach, R. J. Massey, and F. Hamel, Cleavage of vasoactive intestinal peptide at multiple sites by autoantibodies, *J. Biol. Chem.*, 266: 16128–16134 (1991)). Amino acid composition analysis was after hydrolysis of samples at 110° C. in 6 normal HCl using a Beckman 6300 analyzer. Mass spectrometry was done using a Bruker benchtop linear time-of-flight mass spectrometer. Ionization was accomplished by matrix-assisted laser desorption ionization with a nitrogen laser (337 nm) with α-cyanohydroxycinnamic acid as the matrix. The samples were dissolved in 3:1 water:acetonitrile containing 0.1% trifluoroacetic acid. Approximately 1–5 pmol of samples were placed on the probe tip with a 10,000-fold excess of the absorbing matrix.

IV. Assay Results

Pro-phe-arg-MCA hydrolysis by IgG purified from 30 healthy humans and 30 rheumatoid arthritis patients (supplied by Dr. J. O'dell, Chief, Rheumatology Section, Univ. Nebr.) was compared. A decrease in activity in the patient samples was evident. See FIG. 1. VIP-hydrolysis by the control and rheumatoid arthritis IgG samples was essentially equivalent (not shown), ruling out sample-preparation artifacts. Tg-specific antibodies and a recombinant anti-VIP light chain display a similar antigen-nonspecific hydrolytic activity. The data on rheumatoid arthritis patients demonstrate a decrease in nonspecific catalytic immunity in this disease. The activity in the rheumatoid arthritis patients was significantly lower (P<0.0001, 2-tailed Mann-Whitney U-test). Variations in catalytic activity have been attributed to release of small amounts of free light chain subunits from IgG preparations held at low concentrations (Paul S., M. Sun, R. Mody, H. K. Tewary, S. Mehrotra, T. Gianferrara, M. Meldal, and A. Tramontano, Peptidolytic monoclonal antibody elicited by a neuropeptide, *J. Biol. Chem.*, 267: 13142–13145 (1992); and Li, L., and S. Paul, Low-level, spontaneous formation of peptidolytic antibody fragments, *FASEB J.,* 8: 1369 (1994) (Abstr.).

EXAMPLE II

ANTIGEN SPECIFIC CATALYTIC ANTIBODIES
A. Human anti-thryroglobulin antibodes Autoantibodies to thyroglobulin (Tg), a 660 kD dimer of identical subunits, are found in more than 90% of patients with Hashimoto's thyroiditis (Weetman, A. P., Autoimmune thyroiditis: Predispositon and pathogenesis, *Clin. Endocrinol.,* 36: 307–323, 1992; and Bigazzi, P. E. and N. R. Rose, Autoimmune thyroid disease, In: *The Autoimmune Diseases,* edited by N. R. Rose and I. R. Mackay. Orlando, Fla.: Academic Press, Inc. 1985, pp.161–199). Adoptive transfer of anti-Tg antibodies alone is reported to induce thyroiditis (Clagett, J. A., C. B. Wilson, and W. O. Weigle, Interstitial immune complex thyroiditis in mice, The role of autoantibody to thyroglobulin, *J. Exp. Med.,* 140: 1439–1456, 1974; and Tomazic, V. and N. R. Rose, Autoimmune murine thyroiditis. VII, Induction of the thyroid lesions by passive transfer of immune serum, *Clin. Immunol. Inmunopathol.,* 4: 511–518, 1975). Autoantibodies combined with lymph node cells from animals immunized with Tg transfer the disease more effectively than the cells alone (Rose, N. R., M. F. Molotchnickoff, and F. J. Twarog, Factors affecting transfer of experimental autoimmune thyroiditis in rats, *Immunology.,* 24: 859–870, 1973). In mice implanted with anti-Tg antibody secreting hybridomas, the thyroid shows histological evidence of antibody-mediated damage (Yokochi, T., Y. Inoue, M. Fukada, M. Kawai, K. Yoshikawa, Y. Suzuki, and N. Kato, Histological and functional changes in the thyroid glands of mice implanted with hybridomas secreting monoclonal autoantibody against mouse thyroglobulin, *Autoimmunity.,* 10: 125–131, 1991). Anti-Tg antibodies are clearly important in causing tissue damage in autoimmune thyroiditis but their mechanism of action remains to be defined. The toxicity of anti-Tg antibodies could derive from their catalytic activities. Anti-Tg antibodies do not fix complement (Adler, T. R., G. N. Beall, J. G. Curd, D. C. Heiner, and U. K. Shabharwal. Studies of complement activation and IgG subclass restriction of anti-thyroglobulin, *Clin. Exp. Immunol.,* 56: 383–389, 1984) (probably because antigenic epitopes on Tg are too widely-spaced) or participate in antibody-dependent cellular cytotoxicity (Bogner, U., H. Schleusener, and J. R. Wall, Antibody-dependent cell mediated cytotoxicity against human thyroid cells in Hashimoto's thyroiditis but not Graves' disease, *J. Clin. Endocrinol. Metab.,* 59: 734–738, 1984).

Figure 2:
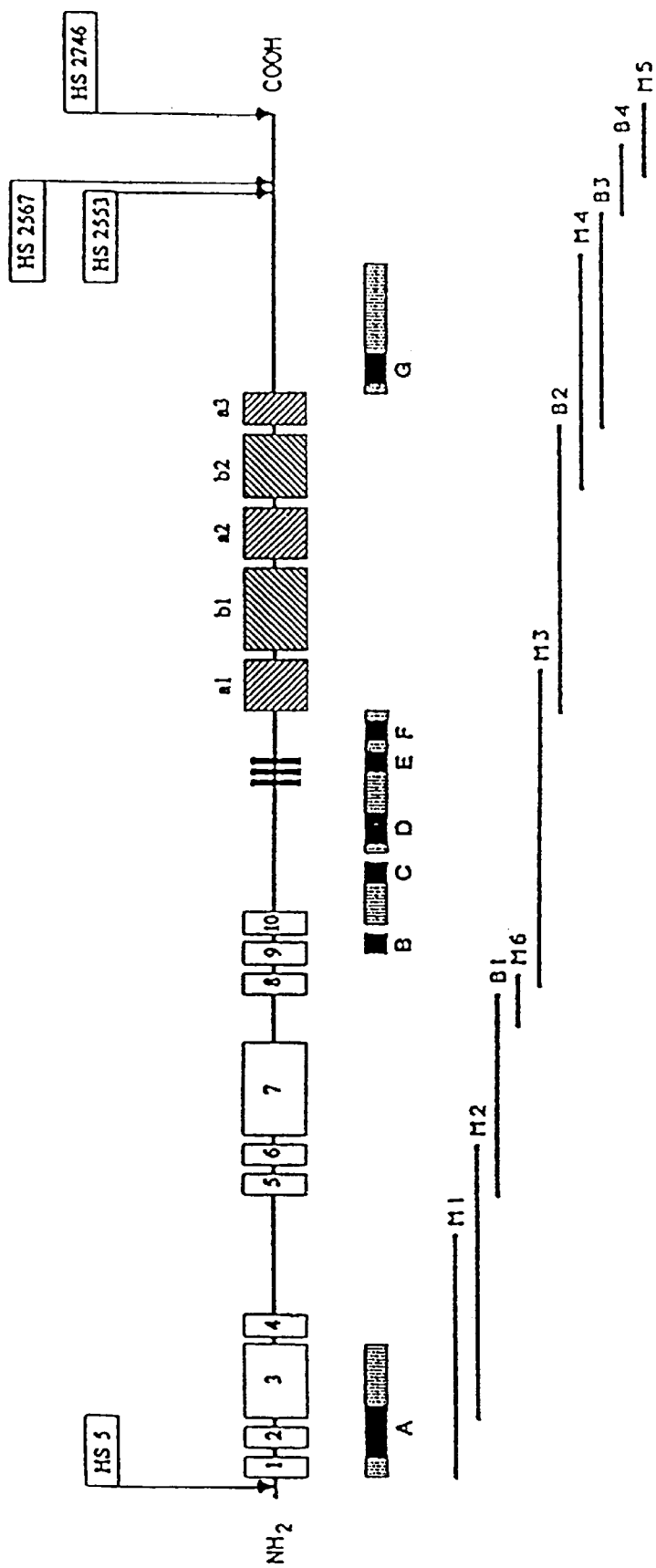
FIG. 2 is a schematic drawing of a human thyroglobulin (Tg) monomer showing the three types of internal homologies (blank, black and hatched boxes). HS (hormogenic sites) are shown by arrows indicating their position on the peptide chain (Malthiery et al., FEBS Letts 279:190, 1991).

Tg is amongst the largest known proteins. It contains three types of repeat domains (Mercken, L., M. J. Simons, S. Swillens, M. Massaer, and G. Vassart, Primary structure of bovine thyroglobulin deduced from the sequence of its 8,431-base complementary DNA, *Nature,* 316: 647–651, 1985) and multiple antigenic epitopes reactive with autoantibodies (Dong, Q., M. Ludgate, and G. Vassart, Towards an antigenic map of human thyroglobulin: identification of ten epitope-bearing sequences within the primary struccture of thyroglobulin, *J. Endocrinol.,* 122: 169–176, 1989; and Rose, N. R., H. S. Bresler, C. L. Burek, S. L. Gleason, and R. C. Kuppers, Mapping the autoepitopes of thyroglobulin, *Isr. J. Med. Sci.* 26: 666–672, 1990). See FIG. 2. Several Tg segments express sequence similarity to acetylcholinesterase (Schumacher, M., S. Camp, Y. Maulet, M. Newton, K. MacPhee-Quigley, S. S. Taylor, T. Friedmann, and P. Taylor, Primary structure of *Torpedo californica* acetylcholinesterase deduced from its cDNA sequence, *Nature,* 319: 407–409, 1986). Anti-Tg antibodies bind this enzyme (Ludgate, M., Q. Dong, P. A. Dreyfus, H. Zakut, P. Taylor, G. Vassart, and H. Soreq, Definition, at the molecular level, of a thyroglobulin-acetylcholinesterase shared epitope: study of its pathophysiological significance in patients with Graves' opthalmopathy, *Autoimmunity,* 3: 167–176, 1989). Anti-Tg antibodies also bind thyroid peroxidase (Ruf, J., M. Ferrand, J. M. Durand-Gorde, C. De Micco, and P. Carayon, Significance of thyroglobulin and antibodies cross-reactive with thyroperoxidase (TGPO antibodies) in individual patients and immmunized mice, *Clin. Exp. Immunol.,* 92: 65–72, 1993; Ruf, J., M. Ferrand, J. M. Durand-Gorde, and P. Carayon, Immunopurification and characterization of thyroid autoantibodies with dual specificity for thyroglobulin and thyroperoxidase, *Autoimmunity,* 11: 179–188, 1992; and Kohno, Y., N. Naito, Y. Hiyama, N. Shimojo, N. Suzuki, O. Tarutani, H. Nimi, H. Nakajima, and T. Hosoya, Thyroglobulin and thyroid peroxidase share common epitopes recognised by autoantibodies in patients with chronic autoimmune thyroiditis, *J Clin Endocrinol Metab.,* 67: 899–907, 1989) (TPO), a membrane-bound enzyme, presumably because of the presence of a conformationally similar epitope in the two proteins (there is no sequence similarity between Tg and TPO). Tg-antibodies are also observed in subjects without thyroiditis, usually at concentrations lower than in thyroiditis patients. The antibodies in healthy individuals are directed against phylogenetically conserved epitopes, and disease-associated antibodies, against newly evolved species-specific epitopes (Rose, N. R., H. S. Bresler, C. L. Burek, S. L. Gleason, and R. C. Kuppers. Mapping the autoepitopes of thyroglobulin, *Isr. J. Med. Sci.* 26:666–672, 1990). This has lead to suggestions that the antibodies found in healthy subjects play a physiological role in removing excess Tg. Increased Tg-antibody levels are also observed in diabetes, rheumatoid arthritis, Sjögren's syndrome, lupus and certain cancers (Rose, N. R. and I. R. Mackay, Editors, *The Autoimmune Diseases,* Orlando: Academic Press, Inc., 1985; and Bigazzi, P. E. and N. R. Rose. Autoimmune thyroid disease, In: *The Autoimmune Diseases,* edited by N. R. Rose and I. R. Mackay, Orlando, Fla.: Academic Press, Inc. 1985, pp. 161–199). These antibodies are associated with thyroid dysfunction in some but not all patients.

Tg is the precursor of thyroid hormones. Tg is secreted by thyrocytes into the colloid of acini, it undergoes iodination by TPO on the luminal face of thyrocytes, iodotyrosines located in the hormonogenic segments of Tg (Marriq, C., M. Rolland, and S. Lissitzky, Structure-function relationships in thyroglobulin: Amino acid sequence of two different thyroxine-containing peptides from porcine thyroglobulin, *EMBO J,* 1: 397–401, 1982) (the N- and C-terminal regions) are coupled by TPO, hormone-rich Tg is taken up by thyrocytes and proteolyzed, and $T_3$ and $T_4$ are released by the cells (Van Herle, A. J., G. Vassart, and J. E. Dumont, Control of thyroglobulin synthesis and secretion, *N. Engl. J. Med.,* 301: 239–249, 1979). Iodination and coupling of tyr residues by TPO is strictly dependent on recognition of the native conformation of Tg (Lamas, L. and A. Taurog, The importance of thyroglobulin structure in thyroid peroxidase-catalyzed conversion of diiodotyrosine to thyroxine, *Endocrinology,* 100: 1129–1136, 1977; and Turner, C. D., S. B. Chernoff, A. Taurog, and A. B. Rawitch, Differences in iodinated peptides and thyroid hormone formation after chemical and thyroid peroxidase-catalyzed iodination of human thyroglobulin, *Arch Biochem Biophys.,* 222: 245–258, 1983). Binding and hydrolysis of Tg by catalytic antibodies is likely, therefore, to result in reduced thyroid hormone output.

Figure 3:
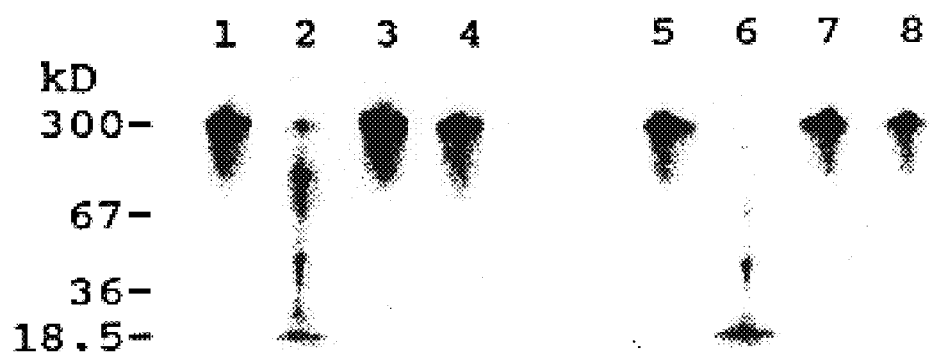
FIG. 3 is an autoradiogram showing the cleavage of radiolabeled $^{125}$I-Tg incubated for 5 hours (lanes 1–4) or 16 hours (lanes 5–8) with Tg-antibodies (lanes 2,6), IgG depleted of Tg-antibodies (lanes 3,7), Tg-antibodies immunoadsorbed with immobilized goat anti-human IgG (lanes 1,5) and diluent without antibodies (lanes 4,8).

For an antigen specific catalytic antibody assay, thyroglobulin (Tg) was radiolabeled with $^{125}$I using chloramine-T. SDS-electrophoresis of $^{125}$I-Tg, followed by autoradiography showed a single radioactive band at 330 kDa, consistent with observations that SDS dissociates native Tg into two identical 330 kDa subunits (Edelhoch, H. and R. F. Lippoldt, The properties of thyroglobulin. II, The effects of sodium dodecyl sulfate, *J. Biol. Chem.*, 235: 1335–1340, 1960). $^{125}$I-Tg was incubated with Tg-specific autoantibodies isolated from a patient with Hashimoto's thyroiditis by protein A-Sepharose and Tg-Sepharose chromatography (code DEM; see references 58 and 105 for antibody binding characteristics). This resulted in disappearance of the 330 kD Tg monomer and formation of a major 15 kD product and minor 125 kD, 60 kD and 25 kD products indicating that the antibodies must cleave several peptide bonds in Tg. See FIG. 3. The reaction rate increased linearly with increasing Tg antibody concentrations, estimated from the rate of disappearance of the 330 kD $^{125}$I-Tg band. Background $^{125}$I-Tg hydrolysis in buffer without antibodies was not detected. IgG depleted of Tg-specific antibodies (IgG in the unbound fraction from the Tg-Sepharose column) did not hydrolyze $^{125}$I-Tg.

The composite kinetics of Tg-antibody activity were computed from initial rate data obtained at increasing concentrations of Tg. The deduced K. value (39 nM) is remarkably low and consistent with high affinity Tg recognition by the antibodies. The reaction rate ($k_{cat}$) is slow, but by virtue of efficient substrate recognition, the antibody kinetic efficiency ($k_{cat}/K_m$) is in the range observed for conventional proteases. A murine anti-Tg monoclonal antibody with Tg-hydrolyzing activity has also been identified, which cleaves Tg with about 10-fold lower potency than the autoantibodies.

Antibody hydrolytic specificity was characterized using stable peptide-MCA conjugates as substrates. Cleavage of the amide bond between the peptide carbonyl and the leaving group (aminomethylcoumarin) is accompanied by increased fluorescence. These conjugates serve as substrates for a variety of proteases (Sarath, G., R. S. De La Motte, and F. W. Wagner, Protease assay methods, In: *Proteolytic Enzymes a Practical Approach*, edited by R. J. Beynon and J. S. Bond. Oxford, UK: IRL Press 1989, pp.25–55). The natural substrate, Tg, is unsuitable for analyzing specificity because it contains multiple antibody reactive epitopes and internally homologous domains (Mercken, L., M .J. Simons, S. Swillens, M. Massaer, and G. Vassart, Primary structure of bovine thyroglobulin deduced from the sequence of its 8,431-base complementary DNA, *Nature.*, 316: 647–651, 1985; Dong, Q., M. Ludgate, and G. Vassart, Towards an antigenic map of human thyroglobulin: identification of ten epitope-bearing sequences within the primary struccture of thyroglobulin, *J. Endocrinol.*, 122: 169–176, 1989; and Rose, N. R. , H. S. Bresler, C. L. Burek, S. L. Gleason, and R. C. Kuppers, Mapping the autoepitopes of thyroglobulin, *Isr. J. Med. Sci.*, 26: 666–672, 1990). Three tripeptide substrates containing MCA linked to a basic residue were cleaved by the antibodies. Other than the presence of arg-MCA or lys-MCA bonds, there is no similarity in the sequences of these substrates. Single amino acid-MCA conjugates did not serve as antibody substrates. In a control immunoadsorption experiment, Tg-autoantibodies (8 µg protein) were incubated with goat anti-human IgG (H+L conjugated to Sepharose 4B. The supernatant was recovered and the gel eluted with 0.5 ml aliquots of 0.1 M glycine-HCl, pH 2.7, the eluates neutralized with 1 M Tris base and assayed for hydrolytic activity. Essentially all of the Tg-autoantibodies were bound by the gel, determined by SDS-electrophoresis and silver-staining and quantitative scanning of the intensities of IgG bands (Paul, S., D. J. Volle, and M. Sun, Affinity chromatography of catalytic autoantibody to vasoactive intestinal peptide, *J. Immunol.*, 145: 1196–1199, 1990). The unbound antibodies displayed little or no $^{125}$I-Tg hydrolyzing (FIG. 3) and peptide-MCA hydrolyzing activities. Antibodies eluted from the anti-IgG matrix with the low pH buffer displayed essentially the same specific pro-phe-arg-MCA hydrolyzing activity (43.5 FU/µg/h) as the starting Tg-antibody fraction (48.7 FU/µg/h).

The hydrolysis of increasing concentrations of pro-phe-arg-MCA by the Tg-specific antibodies was consistent with Michaelis-Menten kinetics. At saturating concentrations of this substrate (0.3 mM), the antibodies (30 nM) hydrolyzed 2.1 µM substrate over 18 h, indicating multiple turnovers characteristic of a true catalyst. The $K_m$ value for pro-phe-arg-MCA hydrolysis was 436-fold greater than that for Tg hydrolysis, consistent with low affinity recognition of the former substrate by the antibody catalytic site.

Figure 4:
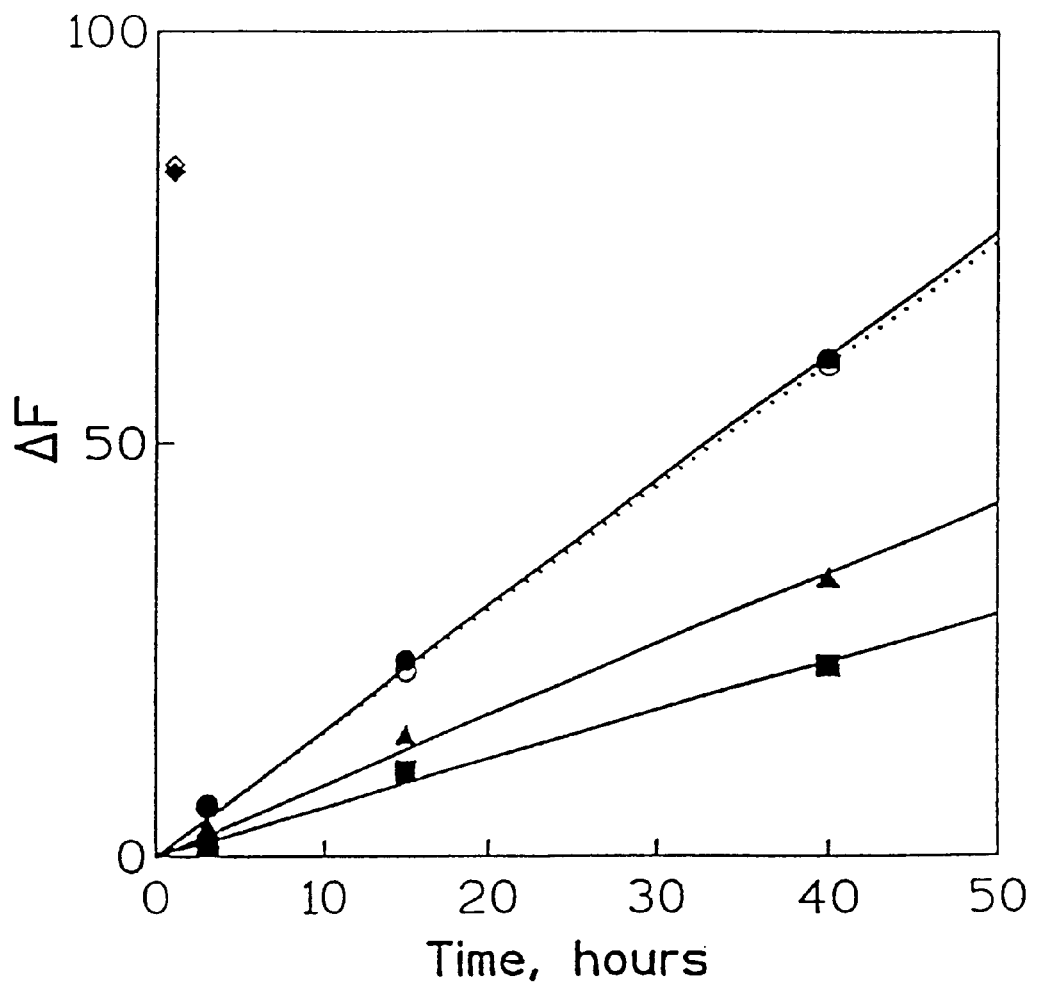
FIG. 4 is a graph showing progress curves of peptide-methylcoumarinamide (MCA) (60 μM) hydrolysis by Tg-antibodies (10 nM) in the absence (—●—) and presence of 100 nM albumin (—○—), 10 nM Tg (—▲—) or 100 nM Tg (—■—).

Nanomolar concentrations of Tg inhibited the hydrolysis of pro-phe-arg-MCA by the antibodies. See FIG. 4. Equivalent concentrations of albumin, a protein unrelated to the binding specificity of the antibodies, were without effect on antibody activity. Trypsin catalyzed pro-phe-arg-MCA hydrolysis in the presence and absence of Tg was essentially identical, ruling out non-specific Tg effects.

Taken together with previous observations of increased VIP hydrolyzing antibodies in asthma patients (Paul, S., Q. S. Gao, H. Huang, M. Sun, A. Thompson, S. Rennard, and D. Landers, Catalytic antibodies to VIP, 37th Annual Thomas L. Petty Aspen Lung Conference, Aspen, Colo. Jun. 8–11, 1994) and DNA-hydrolyzing autoantibodies in lupus patients (Shuster, A. M., G. V. Gololobov, O. A. Krashuk, and A. G. Gabibov, Anti-idiotype and natural catalytically active antibodies, *Mol Biol.* 25: 478–485, 1991), the demonstration of catalysis by Tg-specific autoantibodies from a patient with Hashimoto's thyroiditis points to a pathophysiological role for catalytic antibodies in autoimmune disease. The kinetic properties of the Tg-autoantibodies described here suggest two potential mechanisms of action. First, since the catalytic autoantibodies recognize Tg with high affinity, they may selectively deplete Tg. Second, large deposits of thyroglobulin found in the thyroid are likely to result in homing of the autoantibodies to this organ. At elevated intra-thyroidal autoantibody concentrations, the ability to catalyze the breakdown of target substrates unrelated to Tg may cause generalized proteolysis and tissue damage.

B. Human VIP antibodies

High affinity VIP binding autoantibodies are found in subpopulations of healthy subjects who exercise habitually and patients with asthma (Paul, S., P. Heinz-Erian, and S. I. Said, Autoantibody to vasoactive intestinal peptide in human circulation, *Biochem. Biophys. Res. Commun.*, 130: 479–485, 1985; Paul, S. and S. I. Said, Human autoantibody to vasoacive intestinal peptide: Increased incidence in muscular exercise, *Life Sci.*, 43: 1079–1084, 1988; and Paul, S., S. I. Said, A. Thompson, D. J. Volle, D. K. Agrawal, H. Foda, and S. De La Rocha, Characterization of autoantibodies to VIP in asthma, *J. Neuroimmunol.*, 23: 133–142, 1989). Some of these antibodies catalyze the hydrolysis of VIP. Several lines of evidence showed (Paul, S., D. J. Volle, C. M. Beach, D. R. Johnson, M. J. Powell, and R. J. Massey, Catalytic hydrolysis of vasoactive intestinal peptide by human autoantibody, *Science.*, 244: 1158–1162, 1989; Paul, S., M. Sun, R. Mody, S. H. Eklund, C. M. Beach, R. J.

Massey, and F. Hamel, Cleavage of vasoactive intestinal peptide at multiple sites by autoantibodies, *J. Biol. Chem.,* 266: 16128–16134, 1991; and Paul, S., D. J. Volle, and M. Sun, Affinity chromatography of catalytic autoantibody to vasoactive intestinal peptide, *J. Immunol.,* 145: 1196–1199, 1990) that the activity belonged to antibodies: (a) Contamination of overloaded IgG with non-immunoglobulin proteins was not detected by denaturing gel electrophoresis and silver staining; (b) The hydrolytic activity was retained by immobilized protein G, a bacterial protein that binds the $F_v$ region of IgG; (c) Immobilized anti-human IgG adsorbed out 90–100% of the activity; (d) Gel filtration revealed a peak of hydrolytic activity coincident with the IgG protein peak; (e) The hydrolytic activity was present in Fab fragments; (f) Specific antibodies prepared by affinity chromatography of IgG on immobilized VIP exhibited up to 3,000-fold increased hydrolytic activity. The hydrolytic specificity of IgG and affinity-purified antibody from HS-1 was identical [cleavage at gln(16)-met(17)]; (g) The IgG displayed nM $K_m$ values indicative of tighter substrate binding than known proteases.

EXAMPLE III

STATISTICAL EVALUATION OF THE INVERSE RELATIONSHIP BETWEEN ANTIGEN SPECIFIC CATALYTIC ANTIBODIES AND POLYREACTIVE CATALYTIC ANTIBODIES IN AUTOIMMUNE DISEASE

Figure 5:
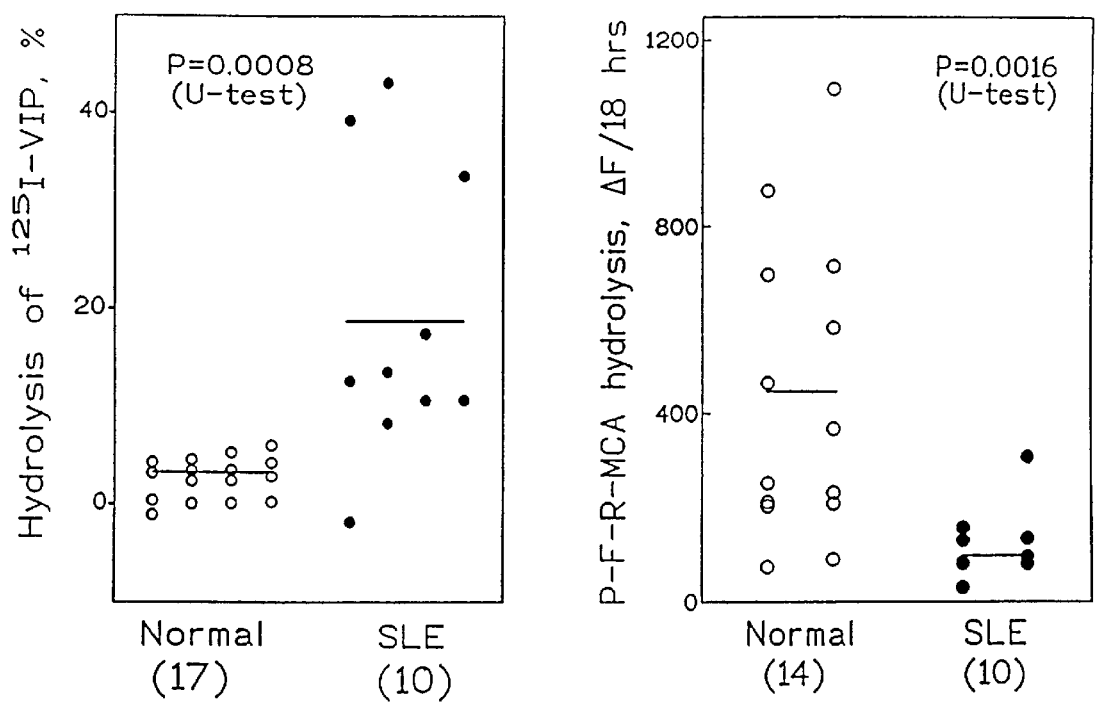
FIG. 5 is a graph illustrating increased VIP cleavage (antigen-specific) and decreased peptide-MCA cleavage (polyreactive) by IgG isolated from SLE patients relative to healthy controls.
Figure 6:
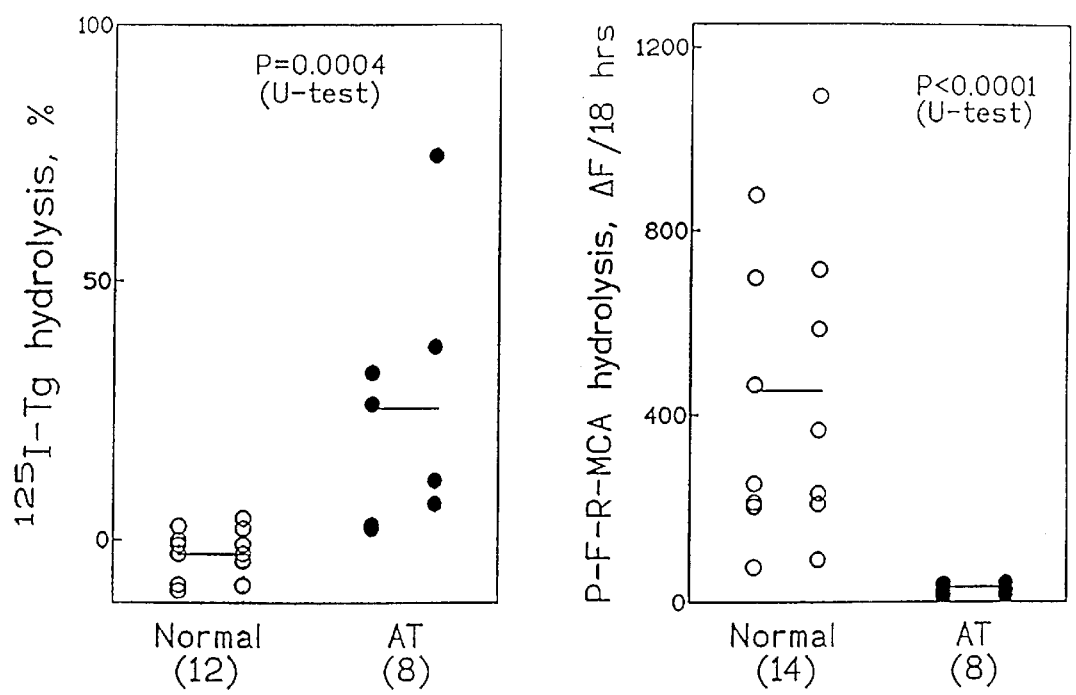
FIG. 6 is a graph illustrated increased Tg cleavage and decreased peptide-MCA cleavage by IgG isolated from autoimmune thyroiditis patients relative to healthy controls.

Hydrolysis of a peptide-MCA substrate, VIP, and Tg by IgG from healthy subjects, SLE patients and autoimmune thyroiditis patients was determined. Decreased peptide-MCA hydrolysis was evident in the SLE and autoimmune thryroiditis patients (P<0.002). See FIGS. 5 and 6. The SLE patients showed increased hydrolysis of VIP as shown in FIG. 5, (P<0.001) and the autoimmune thyroiditis patients showed increased hydrolysis of Tg, FIG. 6 (P<0.001). These data demonstrate that increased autoantigen-specific hydrolyzing antibodies in patients with autoimmune disease is accompanied by decreased polyreactive peptide-MCA hydrolyzing antibodies. As discussed previously, rheumatoid arthritis patients also display decreased polyreactive catalytic antibody activity.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for diagnosing autoimmune disease or the predisposition to said disease in a patient, said method comprising:

(a) providing, as a test sample, a specimen of biological fluid from said patient, said specimen being suspected of containing catalytic antibodies;

(b) providing, as a control sample, a specimen of biological fluid from a healthy individual;

(c) contacting a peptide comprising amino acid residues which may be the same or different and include at least one of arginine, lysine or proline, with said test sample and with said control sample;

(d) subjecting said test sample and said control sample, each containing said peptide, to conditions promoting catalytic cleavage of said peptide by any catalytic antibodies present in said samples; and (e) measuring the relative activity of any catalytic antibodies in said test sample and said control sample, as determined by the presence of cleavage products formed from said peptide, the measurement of depressed activity of catalytic antibodies in said test sample relative to said control sample being indicative of autoimmune disease or predisposition to said disease in said patient.

2. A method as claimed in claim 36, wherein said peptide comprises at least one basic amino acid or proline and a detectable label.

3. A method as claimed in claim 2, wherein said peptide is selected from the group consisting of Arg-CA,Arg-Arg-MCA, Pro-Phe-Arg-MCA, Val-Leu-Lys-MCA, Glu-Lys-Lys-MCA and Boc-Ile-Glu-Gly-Arg-MCA.

4. A method as claimed in claim 36, wherein said peptide is conjugated to a detectable label and the relative activity of catalytic antibodies in said samples is measured by detecting the label associated with at least one cleavage product from said peptide.

5. A method as claimed in claim 4, wherein said detectable label is a substance selected from the group consisting of molecules or ions directly or indirectly detectable based on light absorbance, fluorescence, phosphorescence, or luminescence properties; molecules or ions detactable by their radioactive property; and molecule or ions detectable by their nuclear magnetic resonance or paramagnetic properties.

6. A method as claimed in claim 4, wherein said peptide-detectable label is selected from the group consisting of methylcoumarinamide (MCA), biotin, fluorescein, avidin, and rhodamine.

7. A test kit for carrying out a method for diagnosis of autoimmune disease or the predisposition to said disease in a patient, said test kit comprising containers of:

(i) a predetermined amount of a peptide comprising amino acid residues which may be the same or different and include at least one of arginine, lysine or proline; and (ii) a predetermined amount of a reagent for detection of at least one cleavage product of said peptide, the respective amounts of peptide and detection reagent being sufficient for carrying out the method of claim 1.

8. A test kit as claimed in claim 7, wherein said reagent for detection of at least one cleavage product of said peptide is an antibody conjugated with a detectable label, said antibody binding specifically to said at least one cleavage product formed from said peptide.

9. A test kit as claimed in claim 8, wherein said label is an enzyme and said kit further comprises a substrate which produces a spectrally measurable product under the influence of said enzyme.

10. A method for diagnosing autoimmune disease or the predisposition to said disease in a patient, said method comprising:

(a) providing, as a test sample, a specimen of biological fluid from said patient, which specimen is suspected of containing catalytic antibodies;

(b) providing, as a control sample, a specimen of biological fluid from a healthy individual;

(c) contacting an autoimmune disease-associated antigen with said test sample and with said control sample;

(d) subjecting said test sample and said control sample, each containing said autoimmune disease-associated antigen, to conditions promoting catalytic cleavage of said autoimmune disease-associated antigen by any catalytic antibodies present in said samples; and (e) measuring the relative activity of any catalytic antibodies in said test sample and said control sample, as determined by the presence of cleavage products formed from said autoimmune disease-associated antigen, the measurement of elevated activity of catalytic antibodies in said test sample relative to said control sample being indicative of autoimmune disease or predisposition to said disease in said patient.

11. A method as claimed in claim 10, wherein said autoimmune disease-associated antigen is selected from the group consisting of thyroglobulin, vasoactive intestinal peptide, insulin, insulin receptor, glutamate decarboxylase, acetylcholine receptor, thyroid peroxidase, small nuclear RNA, DNA, histones, phospholipids, gastric parietal cell-associated antigens, collagen, IgG, proteinase 3 and pyruvate dehydrogenase.

12. A method as claimed in claim 10, wherein said autoimmune disease-associated antigen is conjugated to a detectable label to provide an antigen-detectable label conjugate, and the relative activity of catalytic antibodies in said sample is measured by detecting the label associated with at least one cleavage product formed from said autoimmune disease-associated antigen.

13. A method as claimed in claim 12, wherein said detectable label is a substance selected from the group consisting of molecules or ions directly or indirectly detectable based on light absorbance, fluorescence, phosphorescence, luminescence or acoustic properties; molecules or ions detectable by their radioactive property; and molecule or ions detectable by their nuclear magnetic resonance or paramagnetic properties.

14. A method as claimed in claim 12, wherein said antigen-detectable label conjugate is selected from the group consisting of $^{125}$I-VIP, $^{125}$I-Tg, $^{125}$I-IgG, $^{125}$I-gp120, fluorescein-VIP, fluorescein-Tg, fluorescein-IgG and fluorescein-gp120.

15. A test kit for carrying out a method for diagnosing autoimmune disease or the predisposition to said disease in a patient, said test kit comprising containers of:

(i) a predetermined amount of an autoimmune disease-associated antigen; and (ii) a predetermined amount of a reagent for detection of at least one cleavage product of said autoimmune disease-associated antigen, the respective amounts of autoimmune disease-associated antigen and said reagent being sufficient for carrying out the method of claim 10.

16. A test kit as claimed in claim 15, wherein said reagent for detection of at least one cleavage product of said autoimmune disease-associated antigen is an antibody conjugated to a detectable label, said antibody binding specifically to said at least one cleavage product formed from said autoimmune disease-associated antigen.

17. A test kit as claimed in claim 16, wherein said label is an enzyme and said kit further comprises a substrate which produces a spectrally measurable product under the influence of said enzyme.

18. A method for diagnosing autoimmune disease or the predisposition to said disease in a patient, said method comprising:

(a) providing, as a test sample, a specimen of biological fluid from said patient, which specimen is suspected of containing catalytic antibodies;

(b) providing, as a control sample, a specimen of biological fluid from a healthy individual;

(c) contacting a peptide, comprising amino acid residues which may be the same or different and include at least one of arginine, lysine or proline, with a first aliquot of said test sample and with a first aliquot of said control sample;

(d) contacting an autoimmune disease-associated antigen with a second aliquot of said test sample and with a second aliquot of said control sample;

(e) subjecting said first aliquot of test sample and said first aliquot of control sample containing said peptide and said second aliquot of test sample and said second aliquot of control sample containing said autoimmune disease-associated antigen to conditions promoting catalytic cleavage of said peptide and said autoimmune disease-associated antigen by any catalytic antibodies present in said aliquots;

(f) measuring the relative activity of any catalytic antibodies in said first aliquot of test sample and said first aliquot of control sample, as determined by the presence of cleavage products formed from said peptide; and (g) measuring the relative activity of any catalytic antibodies in said second aliquot of test sample and said second aliquot of control sample, as determined by the presence of cleavage products formed from said autoimmune disease-associated antigen, the measurement of depressed activity of catalytic antibodies in said first aliquot of test sample relative to said first aliquot of control sample and the measurement of increased catalytic antibody activity in said second aliquot of test sample relative to said second aliquot of control sample being indicative of autoimmune disease or predisposition to said disease in said patient.

19. A method as claimed in claim 18 wherein said peptide comprises a detectable label and is selected from the group consisting of Phe-Arg-MCA, Arg-Arg-MCA, Pro-Phe-Arg-MCA, Val-Leu-Lys-MCA, Glu-Lys-Lys-MCA and Boc-Ile-Glu-Gly-Arg-MCA.

20. A method as claimed in claim 18, wherein said autoimmune disease-associated antigen is selected from the group consisting of thyroglobulin, vasoactive intestinal peptide, insulin, insulin receptor, glutamate decarboxylase, acetylcholine receptor, thyroid peroxidase, small nuclear RNA, DNA, histones, phospholipids, gastric parietal cell-associated antigens, collagen, IgG, proteinase 3 and pyruvate dehydrogenase.

21. A method as claimed in claim 18, wherein said peptide is conjugated to a detectable label to provide an antigen-detectable label conjugate and the relative activity of catalytic antibodies in said first aliquot of said test sample and said control sample is measured by detecting the label associated with at least one cleavage product formed from said peptide.

22. A method as claimed in claim 21, wherein said detectable label is a substance selected from the group consisting of molecules or ions directly or indirectly detectable based on light absorbance, fluorescence, phosphorescence, or luminescence properties; molecules or ions detectable by their radioactive property; and molecule or ions detectable by their nuclear magnetic resonance or paramagnetic properties.

23. A method as claimed in claim 21, wherein said peptide-detectable label conjugate is selected from the group consisting of Arg-MCA, Phe-Arg-MCA, Arg-Arg-MCA, Pro-Phe-Arg-MCA, Val-Leu-Lys-MCA, Glu-Lys-Lys-MCA Boc-Ile-Glu-Gly-Arg-MCA, Leu-biotin, Ala-biotin, Met-biotin, Phe-biotin, Lys-biotin, Arg-biotin, Phe-Arg-biotin, Arg-Arg-biotin, Pro-Phe-Arg-biotin, Val-Leu-Lys-biotin, Glu-Lys-Lys-biotin, and Boc-Ile-Glu-Gly-Arg-biotin.

24. A method as claimed in claim 19, wherein said autoimmune disease-associated antigen is conjugated to a detectable label to provide an antigen-detectable label conjugate, and the relative activity of catalytic antibodies in said second aliquots of said test sample and said control sample is measured by detecting the label associated with at least one cleavage product formed from said autoimmune disease-associated antigen.

25. A method as claimed in claim 24, wherein said detectable label is a substance selected from the group consisting of molecules or ions directly or indirectly detectable based on light absorbance, fluorescence, phosphorescence, or luminescence properties; molecules or ions detectable by their radioactive property; and molecule or ions detectable by their nuclear magnetic resonance or paramagnetic properties.

26. A method as claimed in claim 24, wherein said antigen-detectable label conjugate is selected from the group consisting of $^{125}$I-VIP, $^{125}$I-Tg, $^{125}$I-IgG, $^{125}$I-gp120, fluorescein-VIP, fluorescein-Tg, fluorescein-IgG and fluorescein-gp120.

27. A test kit for carrying out a method for diagnosing autoimmune disease or the predisposition to said disease in a patient, said test kit comprising containers of:

(i) a predetermined amount of a peptide comprising amino acid residues selected from the group consisting of at least one basic amino acid, proline or a combination thereof;

(ii) a predetermined amount of an autoimmune disease-associated antigen;

(iii) a predetermined amount of a reagent for detection of at least one cleavage product of said peptide; and (iv) a predetermined amount of a reagent for detection of at least one cleavage product of said autoimmune disease-associated antigen, the respective amounts of said peptide, said autoimmune disease-associated antigen and said detection reagents being sufficient for carrying out the assay of claim 19.

28. A test kit as claimed in claim 27, wherein said reagent for detection of at least one cleavage product of said peptide is an antibody conjugated with a detectable label, said antibody binding specifically to said at least one cleavage product of said peptide.

29. A test kit as claimed in claim 28, wherein said label is an enzyme and said kit further comprises a substrate which produces a spectrally measurable product under the influence of said enzyme.

30. A test kit as claimed in claim 27, wherein said reagent for detection of at least one cleavage product of said autoimmune disease-associated antigen is an antibody conjugated to a detectable label, said antibody binding specifically to said at least one cleavage product of said autoimmune disease-associated antigen.

31. A test kit as claimed in claim 30, wherein said label is an enzyme and said kit further comprises a substrate which produces a spectrally measurable product under the influence of said enzyme.

32. A method as claimed in claim 1, 10 or 18 carried out for the diagnosis of rheumatoid arthritis.

33. A method as claimed in claim 1, 10 or 18 carried out for the diagnosis of systemic lupus erythematosis.

34. A method as claimed in claim 1, 10 or 18 carried out for the diagnosis of Hashimoto's autoimmune thyroiditis.

35. A method as claimed in claim 1, 10 or 18 carried out for the diagnosis of asthma.

* * * * *

UNITED STATES PATENT AND TRADEMARK OFFICE
CERTIFICATE OF CORRECTION

PATENT NO.    : 6,130,049
DATED         : October 10, 2000
INVENTOR(S)   : Sudhir Paul et al.

It is certified that error appears in the above-identified patent and that said Letters Patent is hereby corrected as shown below:

<u>Column 1,</u>
Line 7, please insert the following paragraph:
-- Pursuant to 35 U.S.C. §202(c) it is acknowledged that the U.S. Government has certain rights in the invention described herein, which was made in part with funds from the National Institute of Health, Grant Number R01 AI 31268. --

Signed and Sealed this

Eleventh Day of March, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,130,049
DATED : October 10, 2000
INVENTOR(S) : Sudhir Paul et al.

It is certified that error appears in the above-identified patent and that said Letters Patent is hereby corrected as shown below:

Column 16,
Lines 9 and 16, please delete claim reference numeral "36" and insert therefor -- 1 --.

Signed and Sealed this

Twenty-sixth Day of July, 2005

JON W. DUDAS
*Director of the United States Patent and Trademark Office*